(12) United States Patent
Mahler et al.

(10) Patent No.: US 10,746,644 B2
(45) Date of Patent: Aug. 18, 2020

(54) VITRO METHOD AND APPARATUS FOR ANALYSING THE BEHAVIOUR OF SUBSTANCES IN SIMULATED PHYSIOLOGICAL ENVIRONMENT

(71) Applicant: Hoffmann-La Roche Inc., Little Falls, NJ (US)

(72) Inventors: Hanns-Christian Mahler, Basel (CH); Dhananjay Jagdish Jere, Basel (CH); Sulabh Patel, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/577,431

(22) Filed: Sep. 20, 2019

(65) Prior Publication Data

US 2020/0025664 A1    Jan. 23, 2020

Related U.S. Application Data

(63) Continuation of application No. 15/504,865, filed as application No. PCT/EP2015/068981 on Aug. 19, 2015, now Pat. No. 10,458,891.

(30) Foreign Application Priority Data

Aug. 20, 2014  (EP) .................................... 14181653
Apr. 30, 2015  (EP) .................................... 15165825

(51) Int. Cl.
   *G01N 13/00*    (2006.01)
   *G01N 33/15*    (2006.01)
   (Continued)

(52) U.S. Cl.
   CPC ............. *G01N 13/00* (2013.01); *G01N 33/15* (2013.01); *G01N 33/558* (2013.01); *G01N 33/559* (2013.01); *G01N 2013/003* (2013.01)

(58) Field of Classification Search
   CPC .. G01N 13/00; G01N 2013/003; G01N 33/15; G01N 33/558; G01N 33/559
   See application file for complete search history.

(56) References Cited

U.S. PATENT DOCUMENTS

| 10,458,891 B2 * | 10/2019 | Mahler ................ G01N 33/559 |
| 2007/0092404 A1 | 4/2007 | Hughes |
| 2015/0247864 A1 | 9/2015 | Mrsny |

FOREIGN PATENT DOCUMENTS

| CN | 101534917 A | 9/2009 |
| JP | H03-205017 | 9/1991 |

(Continued)

OTHER PUBLICATIONS

Ng, Chee Ping et al., "A Perfusable 3D Cell-Matrix Tissue Culture Chamber for In Situ Evaluation of Nanoparticle Vehicle Penetration and Transport", *Biotechnology and Bioengineering*, Apr. 15, 2008, pp. 1490-1501, vol. 99, No. 6, Wiley Periodicals, Inc.

(Continued)

*Primary Examiner* — Paul M. West
(74) *Attorney, Agent, or Firm* — Mintz Levin Cohn Ferris Glovsky and Popeo, P.C.

(57) ABSTRACT

The invention refers to an in vitro method and apparatus for analysing the behaviour of substances in simulated physiological environment. The method comprises the steps of providing a first fluid, a gel matrix and a second fluid, separating the first fluid and the gel matrix by at least one first semi-permeable membrane and separating the gel matrix and the second fluid by at least one second semi-permeable membrane. The method further comprises the steps of injecting a substance into the first fluid, letting the substance migrate from the first fluid through the at least one first semi-permeable membrane, through the gel matrix, through the at least one second semi-permeable membrane (Continued)

and into the second fluid, and determining clearance of the substance from the first fluid.

17 Claims, 6 Drawing Sheets

(51) Int. Cl.
*G01N 33/559* (2006.01)
*G01N 33/558* (2006.01)

(56) References Cited

FOREIGN PATENT DOCUMENTS

| WO | WO-2007/137245 A2 | 11/2007 |
| WO | WO-2007/137245 A3 | 11/2007 |
| WO | WO-2014-053840 A1 | 4/2014 |

OTHER PUBLICATIONS

Xu, Jing et al., "Permeability and Diffusion in Vitreous Humor: Implications for Drug Delivery", *Pharmaceutical Research*, Jun. 1, 2000, pp. 664-669, vol. 17, No. 6.
International Search Report dated Feb. 10, 2016 for International Application No. PCT/EP2015/068981, filed Aug. 19, 2015, 4 pages.
Gajraj, Rhiad Tariq Christopher, "A Study of Drug Transport in the Vitreous Humor: Effect of Drug Size; Comparing Micro-and Macro-scale Diffusion; Assessing Vitreous Models; and Obtaining in Vivo Data" 2012, Thesis, Chemical Engineering and Applied Chemistry, University of Toronto. (Year: 2012).

\* cited by examiner

VITRO METHOD AND APPARATUS FOR ANALYSING THE BEHAVIOUR OF SUBSTANCES IN SIMULATED PHYSIOLOGICAL ENVIRONMENT

CROSS REFERENCE TO RELATED APPLICATIONS

This disclosure is a continuation application of U.S. patent application Ser. No. 15/504,865 filed on Feb. 17, 2017, which is a 35 U.S.C. § 371 national stage entry of PCT/EP2015/068981, which has an international filing date of Aug. 19, 2015, which claims priority to European Patent Application No. 14181653.8 filed on Aug. 20, 2014 and European Patent Application No. 15165825.9 filed on Apr. 30, 2015. The disclosures of the patent applications referenced above are herein incorporated by reference in their entireties.

FIELD

The invention relates to an in vitro method and apparatus for analyzing the behaviour of substances, preferably macromolecules such as for example proteins, in simulated physiological environments. Especially, the invention relates to an in vitro method and apparatus for analyzing the behaviour of substances in simulated eye conditions.

BACKGROUND

For the treatment of macular degeneration or retina diseases such as for example diabetic retinopathy, intravitreal injections of drugs have proven successful. In intravitreal injections a drug formulation is directly injected into the vitreous humor (VH), that is, into the clear gel filling the space between lens and retina of the eyeball of for example humans. This is not least due to the fact that in intravitreal injections the fraction of an administered dose of unchanged drug that reaches the retina is high, thus intravitreal injections usually having high bioavailability.

However, in-vitro tests to study for example stability of a drug formulation in vitreous humor (VH) have proven little useful when simulating real in vivo conditions. VH, when not in its natural environment, degenerates fast and a pH value of VH may increase rapidly due to accumulation of degenerated products in the VH. Thus, tests may not represent the actual situation in an eye of a living person, especially not over long periods of time, such as for example several days. In more recent test systems, the physiological pH value of VH may be stabilized by applying a buffering system. Therein, degradation products are allowed to leave the VH though a semi-permeable membrane into a buffer solution.

However, these systems do not allow to simulate different barrier conditions for drug formulations. Especially, they do not allow to simulate different barrier conditions as for example provided by a posterior segment tissue of an eye.

Thus, there is need for an improved in vitro method and apparatus for simulating physiological environment to analyse the behaviour of substances such as for example macromolecules. Especially, there is need for an in vitro method and apparatus for analyzing long term stability of substances in different simulated physiological environments.

SUMMARY

According to an aspect of the invention, there is provided an in vitro method for analysing the behaviour of a substance in simulated physiological natural environment. The method comprises the steps of providing a first fluid, a gel matrix and a second fluid. The method further comprises the steps of separating the first fluid and the gel matrix by at least one first semi-permeable membrane and separating the gel matrix and the second fluid by at least one second semi-permeable membrane. Yet further steps are injecting a substance into the first fluid, letting the substance migrate from the first fluid through the at least one first semi-permeable membrane, then through the gel matrix, then through the at least one second semi-permeable membrane and then into the second fluid, and determining clearance of the substance from the first fluid.

Arranging a gel matrix between at least a first and at least a second semi-permeable membrane allows to simulate diffusion barriers for substances and diffusion of the substance through said barriers in a realistic manner. The gel matrix is arranged between a first fluid where a substance, for example a molecule, for example a macromolecule such as a protein or a drug formulation, is injected into and a second fluid serving as buffer solution. The first fluid corresponds to or simulates the liquid or tissue the substance is injected into. The first fluid may be a fluid extracted from human or animals but may also be an artificial fluid simulating such a natural fluid. The second fluid serves as buffer solution, such that for example a pH value of the system may be kept at desired values, for example be kept constant. The second fluid may serve as reservoir for receiving or absorbing precipitation or degradation products.

The special arrangement allows to simulate different barrier conditions of the same but also of different physiological systems. For example, with injection of a drug formulation into vitreous humor, the formulation's stability and bioavailability may be simulated, for human but also for animal eyes. For example, different diffusion and precipitation behaviour may be tested for, for example, different proteins in different eye conditions (corresponding to more or less degenerated eyes, by age or by disease) and for anterior eye tissue and posterior eye tissue and any combination thereof. These tissues have different molecule barrier properties, which may be simulated and tested with the method and apparatus according to the invention by varying the properties of the gel matrix and optionally also the properties of the semi-permeable membranes. In addition, more realistic test results may be achieved, especially on stability and bioavailability of a substance, for example a protein or a drug formulation, by taking into account a distance between an effective injection location and the location of a diffusion barrier, as well as the physical and chemical environment present at the injection location. Thus, the method and apparatus according to the invention allows to more realistically simulate the geometry of a natural environment, most preferably of an eye environment. This is enabled by the special arrangement of fluids and gel matrix and the arrangement of the apparatus as will be described in detail further below.

The method and apparatus according to the invention may be applied but are not limited to stability assessments, for example concentration dependent precipitation of substances such as for example drug formulations, macromolecules, proteins and/or excipients or combinations thereof; interactions of substances such as for example macromolecules and/or excipient in a specific fluid environment, for example proteins in vitreous humor; stability of a substance upon dilution in a specific fluid, for example vitreous humor and after loss of stabilizing excipients, for example surfactants, sugars, buffering species and tonicity agents; and long term stability in simulated physiological environment, for example eye environment.

In the following, the method and apparatus generally refers to the testing of substances, especially of macromolecules in simulated eye environment. Accordingly, in a preferred embodiment of the method the first fluid is vitreous humor and the second fluid is a buffer solution, preferably a physiologically relevant buffer solution. However, the method and apparatus is not limited to these applications. For example, also a blood-brain barrier may be simulated to test for example stability and bioavailability of substances in brain tissue, when the substances are injected for example into a blood vessel. In that case, the first and second fluid could be blood and cerebrospinal fluid or fluids simulating blood and simulating cerebrospinal fluid.

'Substance' as used in this application may refer to any substance that may be injected into a fluid and that shall be analysed in view of its stability or bioavailability in the method or in the apparatus according to the invention. A substance may be molecules, for example macromolecules such as proteins, antibodies, antibody fragments, fusion proteins, bispecific antibodies, conjugated proteins, natural or synthetic peptides or oligonucleotides, natural or synthetic molecules such as small molecule drugs, sugars, surfactant, buffers, polymers, or any commonly used excipients. Preferably, a substance is a drug formulation such as, for example, a solution, suspension or emulsion, which may also be comprised in a solid matrix or in any other delivery system as described herein below.

'Vitreous humor' as used in this application may be from natural or artificial sources. Natural vitreous humor may be from various animal species, for example porcine, bovine, canine, feline, from rabbits and non-human primates or may be human. Natural vitreous humor may for example be gained from eyes that have previously been removed. Artificial vitreous humor preferably mimics human vitreous humor. Artificial vitreous humor may be prepared from various polymeric materials, for example natural polymers such as but not limited to hyaluronic acid, alginate, agar, chitosan, gelatin, xanthan gum, pectins, collagen, or for example synthetic polymers such as but not limited to pluronic gel, polyvinyl alcohol, polyphosphazenes, any dimeric, trimeric or multimeric gelling polymers composed of PEG, PCL, PLA, PGA, PLGA, poly acrylamide, polyacrylic acid, as well as combinations of these polymers at different concentrations.

Vitreous humor may also be a mixture of artificial and natural vitreous humor or their components in different combinations.

'Gel matrix' as used in this application is a fluid or semi-fluid (having properties in between a solid and a liquid) with predefined but variable viscosity and predefined but variable concentrations of compounds of gel matrix material. Preferably, the gel matrix is a viscous liquid. The gel matrix represents the core of the simulated barrier and is sandwiched between the at least one first and at least one second semi-permeable membrane. Preferably, the at least one first and at least one second semi-permeable membrane are two single semi-permeable membranes, preferably dialysis membranes. However, they may also be multiple semi-permeable membranes, wherein more than one, preferably two, membranes are arranged above each other. Specifications of the barrier may be changed and adapted to varying test conditions by varying the physical and/or chemical characteristics of the gel matrix. For the gel matrix, different polymeric materials of natural or artificial origin may be utilized individually or in combinations at different concentrations. Natural polymers with chemical modifications may be utilized to prepare the gel-matrix. Natural, semi-synthetic and synthetic polymers may be used in different combination and concentrations for the preparation of gel-matrix. The gel matrix may be prepared from various polymeric materials, for example natural polymers such as but not limited to hyaluronic acid, alginate, agar, chitosan, gelatin, xanthan gum, pectins, collagen, or for example synthetic polymers such as but not limited to pluronic gel, polyvinyl alcohol, polyphosphazenes, any dimeric, trimeric or multimeric gelling polymers composed of PEG, PCL, PLA, PGA, PLGA, poly acrylamide, polyacrylic acid, as well as combinations of these polymers at different concentrations.

In some preferred embodiments of the method according to the invention, the Molecular Weight Cut Off (MWCO) of the at least one first or of the at least one second semi-permeable membrane or of both membranes is varied. In some preferred embodiments of the method according to the invention, the composition of the gel matrix is varied, preferably by varying a viscosity of the gel matrix or varying a concentration of a compound of the gel matrix. In some preferred embodiments of the method according to the invention both, the MWCO of at least one of the membranes and the composition of the gel matrix is varied. By these measures, diffusivity through the membranes and/or permeability of the substance through the gel matrix may be altered. Interaction of the substance within the first fluid, with the gel matrix material and their influence on the substance's stability, compatibility and suitability may be studied.

'Buffer solution' is a solution preferably having or being able to maintain a pH value of the system, for example between pH 5.5 and pH 8.5, preferably between about pH 7.0 and about pH 7.6, more preferably at pH 7.4. 'Physiologically relevant buffer solution' is a solution preferably having or being able to maintain a pH value of the system between about pH 7.0 and about pH 7.6, more preferably at pH 7.2-7.4. Preferably, a buffer solution comprises salts. The buffer solution may for example be a phosphate buffered saline (PBS), a bicarbonate buffer, Ringer's bicarbonate buffer, Ringer's lactate buffer, simulated body fluids, other isotonic solutions, cell culture medias, and any other physiologically representative buffers. The fluids used as buffer may also be used for the preparation of the gel matrix in combination with the above mentioned gel matrix materials.

In the present application 'clearance of a substance from a fluid', such as the first fluid, is understood to include the diffusion of the substance out of the fluid, into which the substance has been injected. However, clearance also includes physical or chemical changes of the substance, such as for example a decomposition or precipitation of the substance in the fluid or in any other part of the system, for example in the gel matrix or in the second fluid. Thus, clearance of the substance of the first fluid includes information on, for example, stability and bioavailability of the substance in the respective fluids and in the entire simulated physiological environment.

With the method according to the invention, it is not only possible to analyse the behaviour of an injected substance, such as for example a protein or an excipient. With the method according to the invention, it is also possible to monitor for example decomposition or physical and chemical changes of the first fluid or any other fluid occurring upon injection of the substance into the first fluid and diffusion out of the first fluid into the other fluids.

According to an aspect of the method according to the invention, the step of determining clearance of a substance from the first fluid is performed by measuring a substance concentration in the first fluid, in the second fluid or in both, the first and the second fluid. This may, for example, be done by taking a sample of the respective fluids and having them analysed for their substance content or decomposition products. Analysis may be performed by spectroscopy, for example fluorescence spectrometry, Raman spectroscopy or Ultraviolet-visible spectroscopy. Analysis of fluid samples may also be performed by liquid or gas chromatography, for example size exclusion high performance liquid chromatography (SE-HPLC) or ion exchange high performance liquid chromatography (IE-HPLC). Analysis may also be performed by light scattering methods, for example, static light scattering, dynamic light scattering or turbidimetry. Preferably, concentration measurements or other measurement for clearance determination is performed in a repeated manner, preferably periodically. Preferably, measurements are performed over several hours, more preferably over several days, for example up to one or two weeks or even longer. Duration and intensity of performing measurements may be adapted to the substance, for example a molecule size and permeability of the system. Concentration measurements or other measurements such as for example pH measurements may also be performed by directly placing a probe into the respective to be measured fluid.

According to another aspect of the method according to the invention, the injected substance comprises molecules having a size in a range between about 100 Da and about 400 kDa, preferably, in a range between about 1 kDa and about 250 kDa, for example between 4 kDa and 150 kDa. The specifications of the semi-permeable membranes may be adapted to the sizes and the forms (for example, linear, globular) of the molecules used in the method according to the invention. For example, the Molecular Weight Cut Off (MWCO) of the membranes may be adjusted depending on the desired retention period of a substance in for example the first fluid or for example in the gel matrix. For example, if a substance that shall be analysed consists of or contains smaller molecules, for example smaller than about 10 kDa, then preferably membranes having MWCOs of smaller than or equal to 10 kDa may be used to prolong the retention time (for example up to days). If the retention time shall be reduced (for example to several hours), membranes having MWCOs larger than 10 KDa may be used. Preferably, membranes with MWCOs in a range between about 10 KDa to 100 KDa are used for substances consisting of or containing macromolecules with sizes between about 50 KDa to 150 KDa. Preferably, membranes with MWCOs in a range between about 1 KDa to 50 KDa are used for substance consisting of or containing macromolecules of sizes about 10 KDa.

Preferably, one first semi-permeable membrane and one second semi-permeable membrane is used in the method and apparatus according to the invention. However, instead of one membrane also multiple membranes may be arranged on a support. Preferably, the membranes then are arranged directly next to each other, preferably on top of each other. If several, for example two, membranes are used, the several membranes may have identical MWCOs or may have different MWCOs. By using multiple membranes, specification of the barrier may additionally be altered. Multiple membranes may alter the specification of a barrier not only due to the additional thickness of the multiple membranes but also due to the differing pore size ranges of multiple membranes versus a single membrane (even with the same MWCO). Also the transition from one membrane to the next may contribute to the specification of the barrier due to differing pore locations and sizes the membranes.

Preferably, the specification of the membranes is adapted to a permeability of a real tissue. For example, in some preferred embodiments of the method according to the invention, the at least one first semi-permeable membrane has a Molecular Weight Cut Off (MWCO) substantially corresponding to the Retinal Exclusion Limit (REL). 'Substantially corresponding' is meant to include the REL as well as MWCO values deferring from the REL, for example by up to about 50 percent. The REL is generally known as the maximum size of molecules capable of freely diffusing across the retina of an eye. For a healthy human eye, the REL is defined as being in a range of about 50 kDa ($10^3$ Daltons) to 100 kDa, preferably 70 kDa. However, this range may significantly vary for different species and depending on the status of the eye (alteration due to age, decease etc.). In addition, the REL is highly dependent on the structure of a diffusing molecule, for example, on a linear or globular structure of the molecule.

The semi-permeable membranes used in the method and apparatus according to the invention enable to control the rate of diffusion through the membranes. The semi-permeable membranes are diffusion controlling membranes and may also be considered molecular weight size selective membranes. Preferably, the semi-permeable membranes are dialysis membranes. A dialysis membrane is a semi-permeable film, for example a sheet of regenerated cellulose or cellulose esters, containing various sized pores. Generally, molecules larger than the pores cannot pass through the membrane but small molecules can do so freely. The separation characteristic determined by the pore size-range of a dialysis membrane is referred to as the Molecular Weight Cut Off (MWCO) of the membrane. The diffusion of molecules near the MWCO will be slower compared to molecules significantly smaller than the MWCO. The MWCO of a membrane is not a sharply defined value. Dialysis membranes, depending on the material they are manufactured from, may contain a broad range of pore sizes. Other examples of diffusion controlling membranes are filter membranes with different pore sizes. Generally, membranes with larger MWCO are used when larger molecules are injected into the first fluid and membranes with smaller MWCO are used when smaller molecules are injected into the first fluid. However, the MWCO of a membrane may also be varied to influence residence time of a substance in the first fluid as outlined above. For example, a MWCO may be diminished, when for example a substance shall be retained in the first fluid for a longer period of time, for example for interaction studies of the molecules with the first fluid.

According to a further aspect of the method according to invention, the step of injecting a substance into the first fluid comprises injecting a substance via a substance delivery system into the first fluid. Thereby, the substance is released into the first fluid in a delayed manner. The substance may be injected into the first fluid with the aid of a delivery system, such as for example nanoparticles, microparticles, drug depots (in solid, liquid or gel form), implants that serve as drug depot or external devices that allow a repeated substance delivery with or without repeated injection. In such delivery systems, the substance may be encapsulated, conjugated (attached to a macromolecule) or entrapped in a material or element, which material or element undergoes a physical or chemical change or both (for example, expansion, degradation) over time to release the substance into the fluid the delivery system has been injected into. By the provision of a delivery system, a temporal delay of the release of the substance into the first fluid may be achieved. If migration of the delivery system in the first fluid occurs, the delivery system will move closer to the at least one first semi-permeable membrane before the substance is released and comes into contact with the first fluid. In a real system, with the use of delivery systems, bioavailability may be enhanced by being able to bring substances, for example a drug formulation, closer to its destination location without having to vary the injection location.

In an aspect of the method according to the invention, the method may further comprise the step of growing cells in 2D or 3D cell cultures in a gel matrix layer supported by semi-permeable membranes. For example, commonly used retina cell lines such as ARPE-19, D407, RF-6A. The cells can be grown in culture or co-culture to represent human posterior tissue. The system may be used to study cell-based toxicity and clearance studies of the injected substance or delivery system or cell decomposition.

The method and apparatus according to the invention may not only be adapted to specific test scenarios by the choice of the fluids, gel matrix and semi-permeable membranes. The method and apparatus may also be tailored to analyzing different behaviours of substances in their physiological environment by the geometrical set-up of the above mentioned components, for example, depending on the orientation of the semi-permeable membranes. For example, long-term stability of a molecule, for example a protein or drug formulation, or also, for example, antigen-binding affinities, may best be analysed if a residence time of the respective molecule in a test fluid is sufficiently long. Stability tests and residence times may, for example, give information about how a frequency of administration of a specific drug would have to be chosen. Thus, in some applications it would be desirable to have a residence time of a substance in the first fluid of several days, preferably of several weeks, more preferably of up to a few months. Preferably, during the residence time of a substance in the first fluid, the test conditions remain as close to physiological environment as possible. In the following various embodiments of apparatuses for analyzing the behaviour of molecules in simulated physiological environment are described.

According to a further aspect of the invention, there is provided an apparatus for analyzing the behaviour of molecules in simulated physiological environment. The apparatus comprises a first compartment for receiving a first fluid, a second compartment for receiving a gel matrix, and a third compartment for receiving a second fluid. The apparatus further comprises a first support for supporting at least one first semi-permeable membrane, and a second support for supporting at least one second semi-permeable membrane. The second support is arranged at a distance from the first support. The first support is arranged between the first compartment and the second compartment, and the second support is arranged between the second compartment and the third compartment.

In the apparatus according to the invention, a first fluid in the first compartment may be kept separate from the gel matrix in the second compartment by the at least one first semi-permeable membrane, which is held by the first support. Preferably, the at least one first semi-permeable membrane is arranged on the first support. The at least one first semi-permeable membrane may be arranged on the first support in edge portions of the membrane only. The first support may be designed such that at least one membrane may be arranged on and be supported by substantially an entire area of the first support. The gel matrix is also kept separate from the second fluid in the third compartment by the at least one second semi-permeable membrane, which is held by the second support. Preferably, the at least one second semi-permeable membrane is arranged on the second support. The at least one second semi-permeable membrane may be arranged on the second support in edge portions of the membrane only. The second support may be designed such that at least one membrane may be arranged on and be supported by substantially an entire area of the second support.

The second compartment is mainly formed by the at least one first and the at least one second semi-permeable membrane and possibly also by apparatus side walls. Depending on the embodiment of the apparatus and of the arrangement of the supports, the second compartment is mainly formed by the first support and by the second support and possibly also by apparatus side walls. Preferably, the three compartments are arranged in series. Preferably, the only material exchange occurring between the first and the third compartment are molecules permeating through the at least one first and at least one second semi-permeable membranes and diffusing through the gel matrix.

Preferably, the first, second and third compartment is provided with at least one opening. Preferably, the at least one opening of the compartments corresponds to an at least one opening provided in each of the first and the second support. Preferably, the first and second support are compartment walls provided with the at least one opening. The at least one opening is covered by the respective at least one semi-permeable membrane. In some preferred embodiments, the first support forms a porous wall of the first compartment and of the second compartment and the second support forms a porous wall of the second compartment and of the third compartment. In these embodiments, first and second support are preferably provided with a plurality of openings, which are preferably distributed over the entire area of the supports.

Aspects and advantages of the apparatus have been discussed relating to the method according to the invention and will not be repeated.

According to an aspect of the apparatus according to the invention, the at least one first semi-permeable membrane has a Molecular Weight Cut Off (MWCO) smaller than or equal to the Molecular Weight Cut Off (MWCO) of the at least one second semi-permeable membrane. A larger or equal MWCO of the at least one second membrane theoretically guarantees that all molecules that have passed the at least one first membrane may also pass the at least one second membrane and may be detected in the second fluid. In some preferred embodiments of the method and apparatus according to the invention, the Molecular Weight Cut Off (MWCO) of the at least one first semi-permeable membrane substantially corresponds to the Retinal Exclusion Limit (REL). Preferably, the MWCO of the at least one first membrane is in a range between and including 10 kDa and 100 kDa, especially when simulating eye environment.

According to a further aspect of the apparatus according to the invention, a shape and size of the first support is adapted to the form and size of a retina, preferably a human retina. One or at least one membrane is then arranged on the first support to adopt the form of the first support. By this, a distribution and migration of a substance injected into the vitreous body of an eyeball may be simulated. Especially, distances between the injection location and the retina or also the anterior of an eyeball may be simulated in a realistic manner. Thus, in some preferred embodiments, at least the first support has a concave shape. By this, at least part of the first compartment may simulate the shape of part of an eyeball, which part corresponds to the part of the first compartment formed by the first support. This part is most relevant in view of macromolecule permeation. By a concave (or convex) support and corresponding compartment form, possibly also shapes of other organs may be mimicked in a more realistic manner by the bent surface. Preferably, also the second support has a concave shape, which concave second support may be arranged concentrically to the first support. First and second support are then arranged in parallel to each other and distanced from each other. The second compartment may then substantially entirely be formed by the first and the second support (and the corresponding membranes lying on the respective support).

In such a set-up of the first compartment and at least one first membrane the geometry as well as the physical and chemical environment inside the eyeball is simulated. In combination with the gel matrix and a preferably concave at least one second membrane, the barrier out of the entire tissue covering the eyeball, such as the anterior or posterior eye tissue, may be simulated.

The apparatus, namely the compartment walls and the supports may be made of any material suitable for the fluids and substances used in the apparatus. Preferably, an inert material such as glass, stainless steel, inert metal alloys, inert synthetic plastic or polymer materials is used. Preferably, glass or inert plastics materials are used due to their transparency. Preferably, glass is used as material for the apparatus, due to its inertness and good reutilization properties. In some preferred embodiments of the apparatus according to the invention, the apparatus comprises or is made of glass. Preferably, at least one of the first, second or third compartment, the first support, and the second support comprises or is made of glass. Preferably, all walls of the apparatus including the first and second support are entirely made of glass.

According to another aspect of the apparatus according to the invention, the apparatus further comprises a cover for closing an opening of the first compartment. Through the opening the first fluid may be filled into the first compartment and be removed from same again. Preferably, the closing may be performed in an air-tight manner. By this, ambient influences, such as, for example, humidity or pollution, on the first fluid prior and after substance injection may be kept at a minimum. Preferably, the cover is made of a same material as the apparatus. Preferably, the cover is made of glass.

Embodiments of the apparatus comprising supports for the semi-permeable membranes are particularly favorable for applications with horizontally or substantially horizontally arranged semi-permeable membranes. In a horizontal arrangement of an apparatus, at least two compartments, preferably all compartments are arranged above or on top of each other. Therein, the arrangement of the semi-permeable membranes may be exactly horizontal. However, a horizontal arrangement also includes, for example, a concave or convex form of the membranes simulating a retina or other tissue forms. The supports may support the entire membranes, as well as the weight of the fluid or of the gel matrix acting on the semi-permeable membranes in a horizontal arrangement. An injected substance tends to migrate downwards due to gravitational force. In a substantially horizontal arrangement of the semi-permeable membranes, a semi-permeable membrane basically forms the bottom of the respective compartment. Thus, the substance tends to accumulate on the semi-permeable membrane and may rather directly permeate out of the compartment. It has been found that if accumulation of a substance on the membrane is avoided, this may have an effect on residence time of the substance in the compartment. This may be explained as follows: If the bottom of a compartment is closed, the substance may re-diffuse into the fluid in the compartment until it migrates to the location of the semi-permeable membrane. The semi-permeable membrane may, for example, form a side-wall of the compartment. Such embodiments of the apparatus are favorable for a vertical or substantially vertical arrangement of the semi-permeable membranes. In vertical arrangements, accumulation of substance on the membranes may be avoided or at least limited and a residence time of a substance in the first fluid or also in the gel matrix may be extended.

According to another aspect of the invention there is provided another apparatus for analyzing the behaviour of molecules in simulated physiological environment. The apparatus comprises a first compartment for receiving a first fluid, a second compartment for receiving a gel matrix, and a third compartment for receiving a second fluid. The apparatus further comprises at least one first semi-permeable membrane and at least one second semi-permeable membrane, wherein the at least one second semi-permeable membrane is arranged at a distance from the at least one first semi-permeable membrane. The at least one first semi-permeable membrane is arranged between the first compartment and the second compartment and the at least one second semi-permeable membrane is arranged between the second compartment and the third compartment.

In these embodiments of the apparatus according to the invention, the semi-permeable membranes are arranged in the apparatus without first and second supports. The apparatus may comprise holders for holding the at least one first semi-permeable membrane and the at least one second semi-permeable membrane between the respective compartments. Such holders may, for example, be clamping means or attaching means, where the membranes are clamped or attached to. Preferably, holders are arranged on an external side of the apparatus and do not extend into the apparatus, especially do not extend into any of the compartments. This may simplify the manufacture, set-up and a cleaning of the apparatus. In addition, the semi-permeable membranes may serve as the sole barrier between the fluids and gel matrix in the compartments and no additional mechanical element is present as in the case of first and second support.

According to an aspect of this apparatus according to the invention, the first compartment, the second compartment and the third compartment are arranged in a row, wherein the at least one first semi-permeable membrane and the at least one second semi-permeable membrane are arranged substantially vertically between the respective compartments. In such a vertical arrangement of the semi-permeable membranes the gravitational force acts on the membranes basically along the membranes itself such that supports for the membranes may be omitted. The gel matrix and possibly also the fluids (depending on their density) may also have a supporting effect on the semi-permeable membranes, when arranged side-by side to the membrane. In a substantially vertical arrangement, the arrangement of the semi-permeable membranes may be exactly vertical. However, they may also be arranged at an angle to the exact vertical position. 'Substantially vertical' also includes, for example, a concave or convex form to simulate a portion of an eye ball or other tissue forms to be simulated.

In the substantially vertical arrangement of the semi-permeable membranes, a substance may not accumulate on the membranes as for example in embodiments of the apparatus, where the compartments are arranged above each other. Thus, long-term tests, as for example stability tests in the first fluid, for example vitreous humor, are preferably performed in an apparatus set-up, where gravitational force does not have or only a limited effect on permeability of a substance through a semi-permeable membrane.

Preferably, embodiments of the apparatus without supports are made of glass, however, with the exception of the semi-permeable membranes and preferably also of the holders.

Further aspects and advantages of this further apparatus according to the invention have been described with respect to the method and the apparatus according to the invention comprising supports for the semi-permeable membranes and will not be repeated. In particular, also the further apparatus may be provided with supports, which supports may be shaped and constructed as previously described. With supports, holders may be omitted. Yet further, at least a first support may be concave shaped to simulate the form of the eyeball or retina. Also the specifications and realizations of the semi-permeable membranes may be the same as previously described, for example the specified MWCOs, or the realization of a diffusion controlling membrane, as for example in the form of a single semi-permeable membrane or in the form of an arrangement or combination of two or more semi-permeable membranes.

Preferably, the apparatus according to the invention and as described herein is used for in vitro testing of a substance, preferably a drug formulation, to determine data on stability or bioavailability of the substance, preferably the drug formulation. Preferably, the apparatus according to the invention is used to perform the method according to the invention and as described herein.

BRIEF DESCRIPTION OF THE DRAWINGS

The invention is further described with regard to examples and embodiments, which are illustrated by means of the following drawings, wherein.

DETAILED DESCRIPTION

Figure 1:
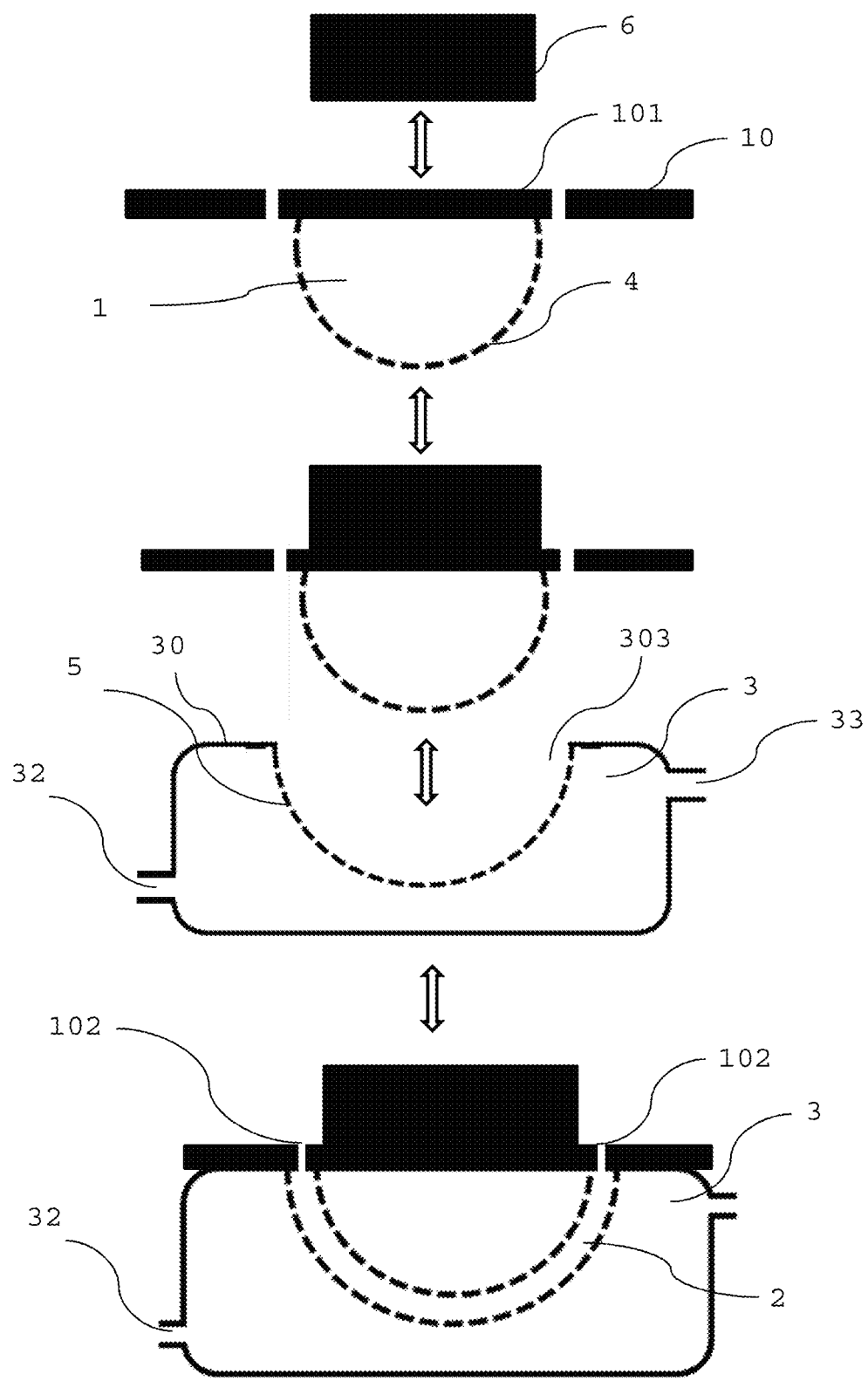
FIG. 1 shows a schematic illustration of a test set-up according to the invention.

In FIG. 1 an embodiment of a set-up of the apparatus and method is schematically shown. The set-up simulates the geometry and situation of an eye and may preferably be used for in vitro tests simulating eye conditions. The first compartment 1 for receiving vitreous humor is formed by an upper wall 10 and a first semi-permeable membrane 4 covering part of said upper wall 10. The upper wall 10 is provided with an opening 101 for filling the first compartment 1 through said opening 101. The opening 101 may be closed, preferably in an air-tight manner, with a cover 6. The cover 6 may for example be a conically shaped plug, for example a glass plug. The semi-permeable membrane 4 has the form of part of a circle, for example ⅔ of a circle. The form of the first compartment 1 and of the first membrane simulates the geometry of an eyeball and retina. The first compartment 1 is mounted to a third compartment 3. Thereby, the first membrane 4 is preferably completely inserted into an upper opening 303 of the third compartment 3 and inside the third compartment 3. The third compartment 3 is for receiving a buffer solution. A concave shaped second semi-permeable membrane 5 is arranged in the upper opening 303 and covers part of an upper wall 30 of the third compartment 3. The second membrane 5 also has the form of part of a circle, for example ½ to ⅔ of a circle. First and second membranes 4, 5 may be supported by respective first and second support forming compartment walls as described below with respect to FIGS. 8a-8e below. In the mounted state of the first and third compartment 1,3, the two semi-permeable membranes 4,5 are distanced from each other forming a second compartment 2 in the gap between the first and the second membrane. Gap sizes may be varied, for example adapted to a physiological system to be simulated. First and second membrane 4,5 are arranged concentrically and such as to have a predefined distance between the membranes, preferably over the entire extension of the membranes. Via inlet and outlet opening 102 provided in the upper wall 10 of the first compartment 1, a gel matrix may be filled into and removed again from the second compartment 2. The three compartments may be sealed, for example by the provision of an O-ring arranged on the upper wall 30 of the third compartment and arranged circumferentially around the gap forming the second compartment 2.

The third compartment 3 is provided with inlet and outlet openings 32, 33. Through the inlet opening the third compartment 3 may be filled with buffer solution and through the outlet opening the third compartment 3 may be emptied. Inlet and outlet are preferably designed to allow a flow through the third compartment such as to clean and replace the content of the third compartment 3. A continuous or discontinuous flow through the third compartment 3 may also be used for sampling the second fluid for subsequent analysis of the sample.

With the first compartment and first membrane 4 the geometry as well as the physical and chemical environment inside an eyeball is simulated. In combination with the gel matrix and second membrane 5, the barrier out of the tissue enveloping the eyeball, such as the anterior or posterior segment tissue, is simulated. A substance, for example macromolecules, may be injected into the vitreous humor in the first compartment 1. It migrates to the first membrane, through the first membrane 4 and the gel matrix in the second compartment 2, through the second membrane and into the buffer solution in the third compartment 3. The removable cover 6 of the first compartment 1, as well as the inlet and outlet 32,33, of the third compartment allow the extraction of samples for analysing purposes.

In the following, examples performed with the system as described in FIG. 1 are described. All experiments mentioned in the examples were performed in aseptic conditions under laminar air flow. Samples were collected from the first and the third compartment 1,3 (or VH-compartment 1 and FT-compartment 3, respectively) at different time intervals.

Example 1

Figure 2:
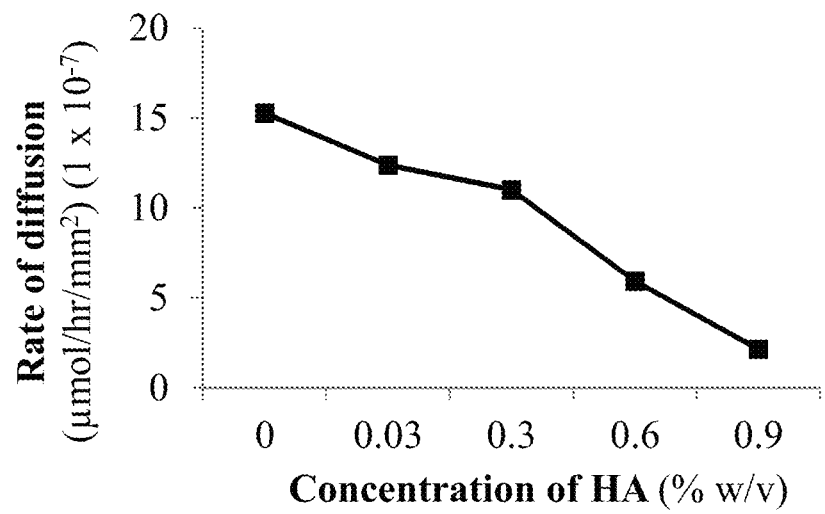
FIGS. 2 and 3 show diffusion rates (FIG. 2) and permeability (FIG. 3) of dextran versus hyaluronic acid concentration in a gel matrix.
Figure 3:
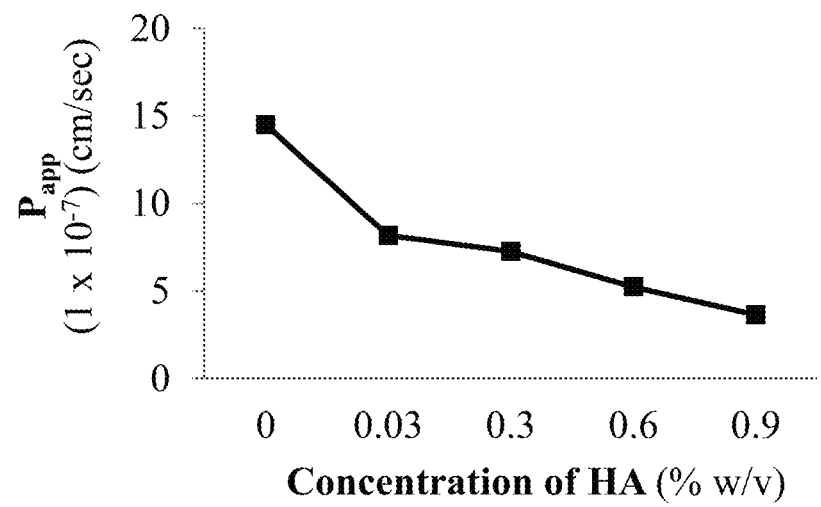

Example 1 was performed in order to optimize a hyaluronic acid gel matrix concentration. For this, impact of different concentrations of hyaluronic acid (HA) (molecular weight $1.4 \times 10^6$ Daltons) gel-matrix (GM) on the diffusion rate of FITC-Dextran (40 kDa) from vitreous humor (VH)-compartment 1 to flow through (FT)-compartment 3 was studied. VH-compartment and FT-compartment were separated by GM-compartment 2, which acts as a diffusion controlling barrier. Two dialysis membranes 4,5 were utilized to separate these three compartments 1, 2, 3. The first dialysis membrane 4 separating VH-compartment 1 from GM-compartment 2 was denoted DM-1 (dialysis controlling membrane 4), and the second dialysis membrane separating GM-compartment from FT-compartment was named DM-2 (dialysis controlling membrane 5). Molecular weight cut-off (MWCO) for DM-1 and DM-2 were 50 kDa and 100 kDa, respectively. FT-compartment 3 was filled with sterile phosphate buffer saline (PBS) (pH 7.4) and GM-compartment 2 was filled with different concentrations of about 3 mL sterile HA gel prepared in PBS (ranging from 0-0.9% w/v). About 3.5 mL of sterile porcine VH was added in VH-compartment. The device was sealed and VH was conditioned overnight at 37° C. At the end of incubation, 50 µL of 80 mg/mL of FITC-Dextran (40 kDa) was injected into the VH-compartment 1. The apparatus was sealed and incubated at 37° C. throughout the study. Samples were evaluated for the concentration of FITC-Dextran by fluorescence spectrophotometer at excitation wavelength of 490 nm and emission wavelength of 520 nm. FIG. 2 illustrates the rate of diffusion versus concentration of HA and FIG. 3 illustrates apparent permeability ($P_{app}$) versus concentration of HA. Permeability is the property of a diffusion controlling barrier (single barrier) to allow transfer of components from one side to the other side of the barrier. When more than one diffusion-controlling barriers are involved, permeability is calculated as apparent permeability (Papp (apparent) or Peff (effective)). In the present experiments, Papp (apparent) has been implemented to facilitate correlation between the in vitro/ex vivo diffusion data with reported in vivo diffusion data in literature. Apparent permeability, for example, can be calculated from the relationship Papp=Q/[A•t•(Co−Ci)], where Q is the quantity of permeant transported through the membrane with the area (A) in time t. Co and Ci are the donor concentration (concentration in the VH chamber) and receiver concentration (concentration in the FT compartment), respectively. Papp can be represented in cm/sec, cm/min or cm/hr.

Results described in FIG. 2 suggest that increase in the concentration of HA gel matrix significantly reduces the rate of diffusion as well as apparent permeability of macromolecule. The plausible explanation could be, increase in the HA concentration may result in reduced porosity of the matrix and/or may increase the interaction of dextran with matrix components resulting in slower diffusion of FITC-Dextran. These results indicate that by changing the GM concentration, it is possible to tune the rate of diffusion of macromolecules across the system.

Example 2

Example 2 was performed in order to analyse the effect of dialysis membranes on the diffusion of macromolecules.

Diffusion of bovine serum albumin (BSA) and Immunoglobulin G (IgG) in the flow direction from VH-compartment to FT-compartment was investigated by varying MWCO of the dialysis membrane. The experiment was performed similarly as described in example 1 with minor modifications. Two different MWCO dialysis membranes were used as DM-1, with MWCO 50 kDa and 100 kDa, whereas the MWCO of DM-2 was kept constant at 100 kDa. VH-compartment was filled with 3.5 mL of sterile porcine VH and GM-compartment was filled with about 3 mL of sterile HA gel (0.6% w/v). FT-compartment was filled with sterile PBS. The device was sealed and VH was conditioned overnight at 37° C. At the end of incubation, 50 µL of FITC-BSA (80 mg/mL) or 200 µL of FITC-IgG (20 mg/mL) was injected into the VH-compartment. The apparatus was sealed and incubated at 37° C. throughout the study. Samples were evaluated for the concentration of FITC-BSA and FITC-IgG by fluorescence spectrophotometer at excitation wavelength of 490 nm and emission wavelength of 520 nm.

Figure 4:
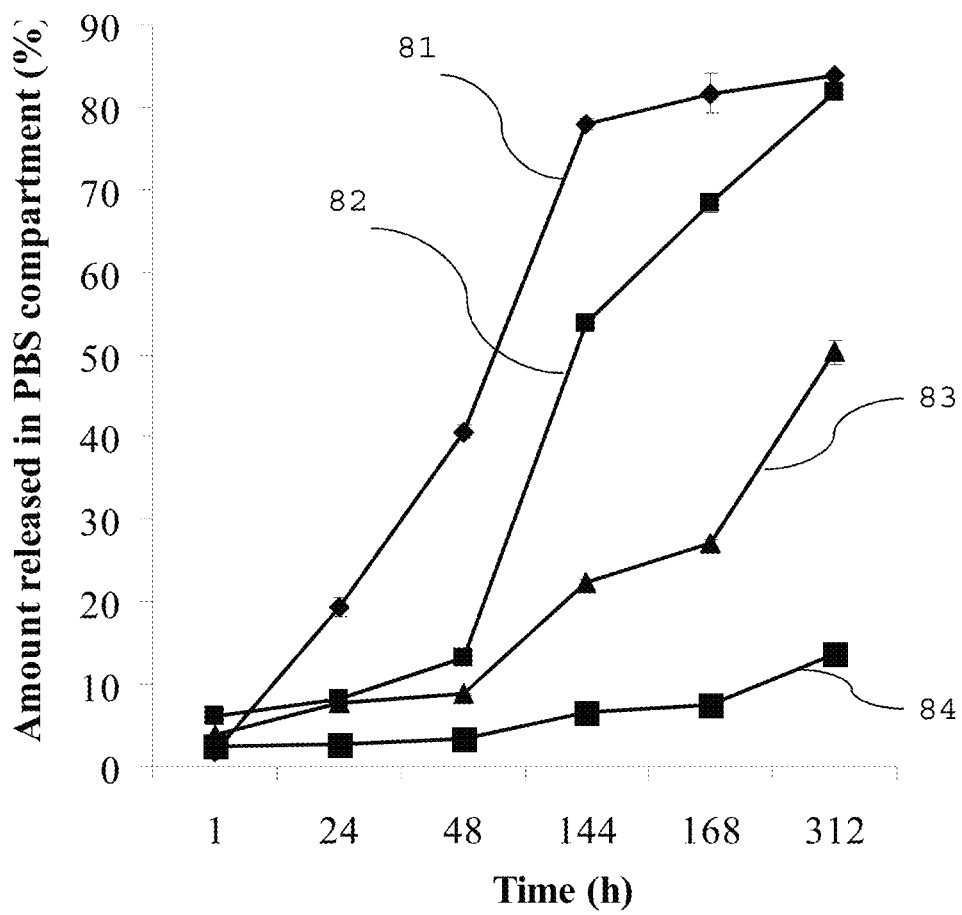
FIG. 4 shows the effect of different membranes on the diffusion of macromolecules versus time.

In FIG. 4 results for diffusion measurements in the FT compartment 3 (named as PBS compartment in the figure) versus time for BSA with DM-1 and DM-2 MWCO 100 kDa 81, of IgG (about 144 kDa) with DM-1 and DM-2 MWCO 100 kDa 82, for BSA with DM-1 50 kDa and DM-2 MWCO 100 kDa 83 and for IgG with DM-1 50 kDa and DM-2 MWCO 100 kDa 84 is depicted. Results shown in FIG. 4 suggest that DM-1 with 50 kDa MWCO (83,84) restrained the diffusion of both IgG and BSA significantly when compared with the diffusion observed with DM-1 with 100 kDa MWCO (81,82). Hence, by changing the dialysis membrane MWCO, it will be further possible to tune the diffusion of macromolecules.

Example 3

Example 3 was performed in order to observe the diffusion of different macromolecules (linear and globular).

This experiment was performed similarly as described in example 1 with minor modifications. 50 kDa MWCO dialysis membrane was used as DM-1 and 100 kDa MWCO dialysis membrane was used as DM-2. VH-compartment was filled with 3.5 mL of sterile porcine VH and GM-compartment was filled with about 3 mL of sterile HA gel (0.6% w/v). FT-compartment was filled with about 35 mL of sterile PBS. The device was sealed and VH was conditioned overnight at 37° C. At the end of incubation, 50 µL of 80 mg/mL of FITC-dextran 4 kDa 91, FITC-dextran 40 kDa 92, FITC-dextran 70 kDa 94, FITC-BSA 93, or 200 µL of FITC-IgG (20 mg/mL) 95 was injected into the VH-compartment. The apparatus was sealed and incubated at 37° C. throughout the study. Samples were evaluated for the concentration of FITC-Dextran by fluorescence spectrophotometer at excitation wavelength of 490 nm and emission wavelength of 520 nm.

Figure 5:
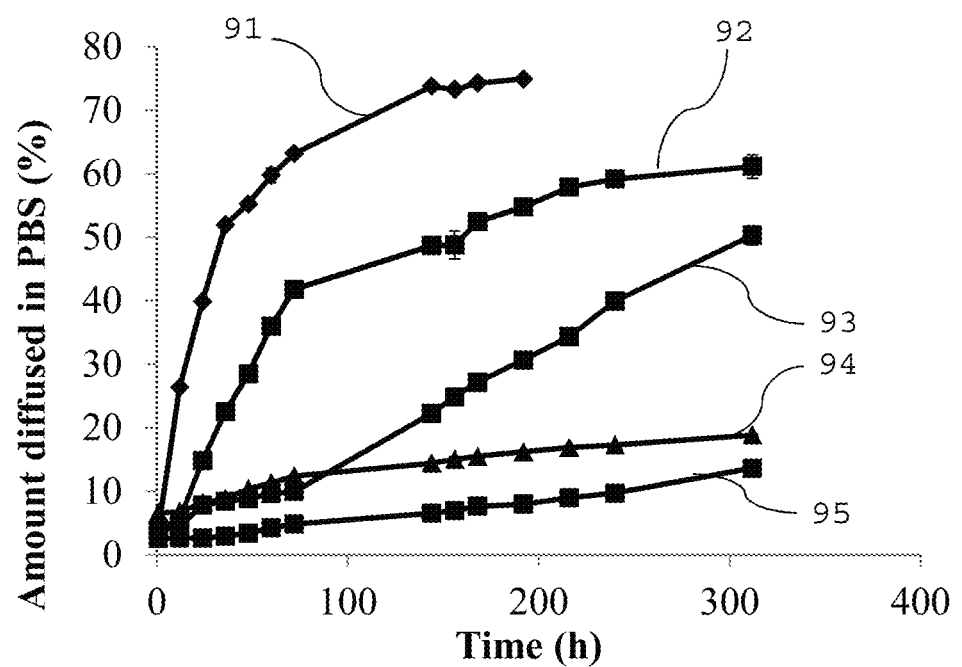
FIGS. 5 and 6 show diffusion (FIG. 5) and permeability (FIG. 6) of various macromolecules.
Figure 6:
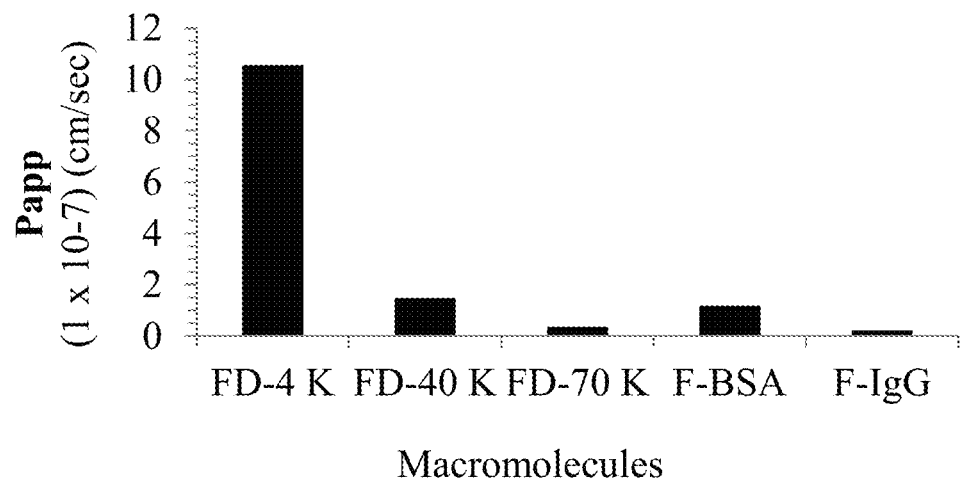

As shown in FIG. 5, where the amount of the different diffused macromolecules versus time is depicted, macromolecules exhibited different rate of diffusion. Smaller molecules diffused at faster rate compared to larger molecules as expected. The same phenomenon was observed for linear and globular kinds of macromolecules. Similarly, smaller molecules exhibited higher $P_{app}$ relative to large molecules, which is depicted in FIG. 6. This may be due to the fact that large molecules face more resistance by the GM due to their higher molecular radius compared to the smaller molecules resulting in low $P_{app}$. Interestingly, FITC-Dextran 40 kDa and FITC-BSA (66 kDa) exhibited similar values of $P_{app}$. Similarity of molecular radius (FITC-Dextran 40 kDa: 4.5 nm, and FITC BSA: 3.62 nm) may attribute to their similar $P_{app}$.

Example 4

In this experiment, diffusion of a monoclonal antibody (mAb1) in the presence or absence of GM was investigated in the direction from VH-compartment to FT-compartment. The experiment was performed similarly as described in example 1 with minor modifications. Again, 50 kDa MWCO dialysis membrane was used as DM-1 and 100 kDa MWCO dialysis membrane was used as DM-2. VH-compartment was filled with 3.5 mL of sterile porcine VH and GM-compartment was filled with about 3 mL of sterile HA gel (0.6% w/v) or sterile PBS (without matrix). FT-compartment was filled with sterile PBS. The device was sealed and VH was conditioned overnight at 37° C. At the end of incubation, 33 µL of mAb1 (120 mg/mL) was injected into the VH-compartment. The apparatus was sealed and incubated at 37° C. throughout the study. Samples were evaluated for the concentration of mAb1 by size exclusion chromatography (SEC).

Figure 7:
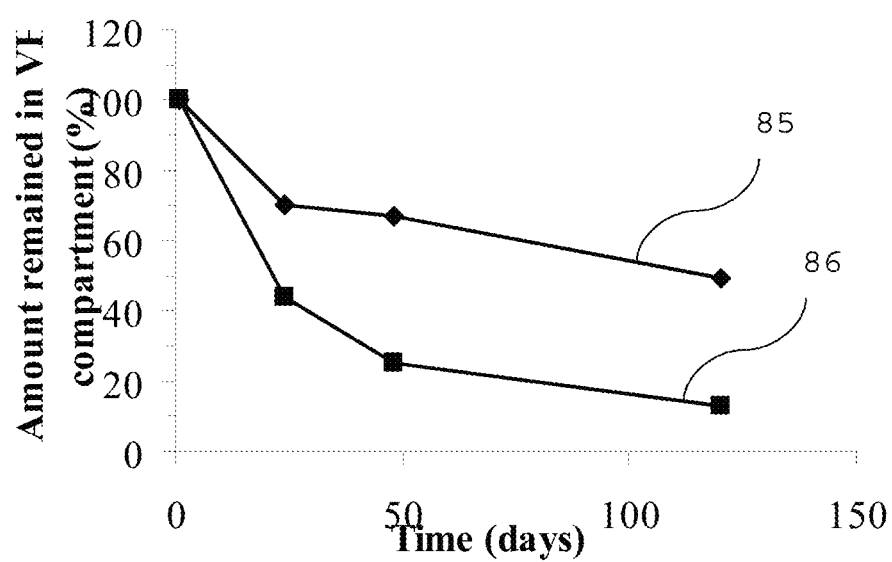
FIG. 7 shows test results performed with monoclonal antibody.

In FIG. 7 the amount of mAB1 in VH compartment versus time is depicted. As shown, diffusion of mAb1 was significantly reduced in the presence of GM (about 51% mAb1 diffused out from VH-compartment at 120 h), indicated by curve 85, when compared to the diffusion observed in absence of GM (about 87% mAb1 diffused out from VH-compartment at 120 h), which is indicated by curve 86. Reduction in the diffusion may be attributed to the resistance provided by the gel-matrix. This result clearly indicates that it is possible to tailor the residence time of protein therapeutics into the VH compartment 1 by altering the concentration of gel-matrix.

Figure 8A:
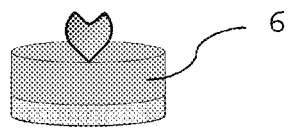
FIGS. 8a-8e show a first illustrative embodiment of an apparatus according to the invention.
Figure 8B:
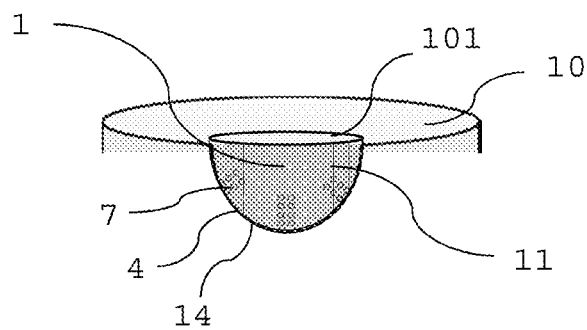
Figure 8C:
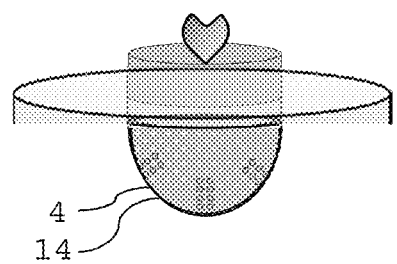
Figure 8D:
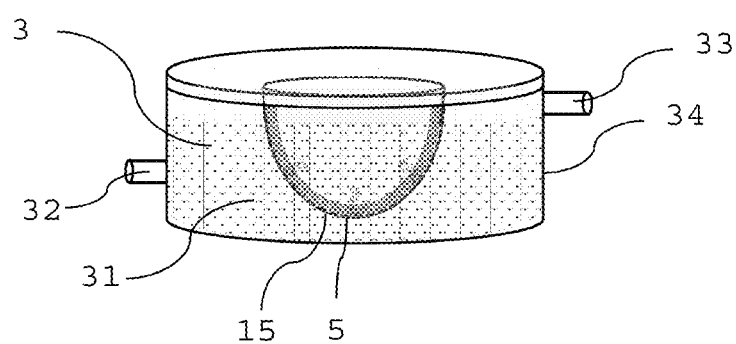
Figure 8E:
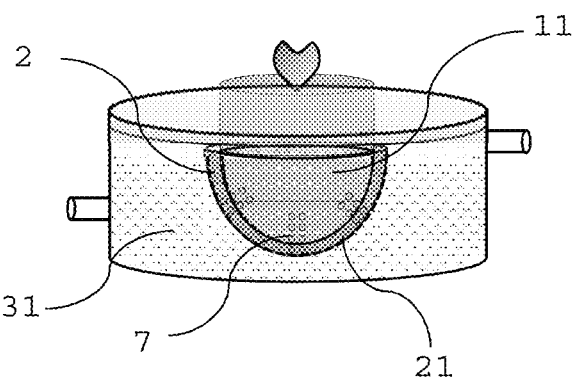

In FIG. 8a to FIG. 8e an illustrative embodiment of an apparatus according to the invention and its parts are shown. The same reference numbers as in FIG. 1 are used for the same or similar features. FIG. 8a shows the cover 6 having a cylindrical form and having a circumference corresponding to the size of the opening 101 in the upper wall 10 of the first compartment 1. When in a mounted state as shown in FIG. 8c, the cover preferably forms an air-tight seal with the upper wall 101. Macromolecules 7, representing a substance, in a first fluid such as vitreous humor 11 are indicated with circles. In FIG. 8c, the macromolecules have already migrated through the first fluid 11, for example vitreous humor, in the first compartment 1 into the direction of the first membrane 4. The first membrane is arranged on a first support forming part of the upper wall 101 of the first compartment 1. In FIG. 8d the second membrane 5 is arranged on a second support 15. The second support 15 forms part of the upper wall 30 of the third compartment 3. The third compartment is cylindrically shaped but may basically have any other form. The third compartment is filled with a second fluid, preferably a physiologically relevant buffer solution 31. Inlet and outlet 33,32 are formed by tube sections attached to or preferably integrated into the side wall 34 of the third compartment 3. First and second support 14, 15 are arranged equidistantly in the mounted state of first and third compartment as shown in FIG. 8e. There, some macromolecules are indicated as having migrated to the first membrane 4, some are shown as having partly passed the gel matrix 21 in the second compartment 2 formed by the first and second membrane 4,5 (supported by the first and second support 14,15) and some are about to diffuse through the second membrane 5.

The three compartments 1, 2, 3, are arranged above or on top of each other. The semi-permeable membranes 4,5 are arranged substantially horizontally between the respective compartments forming a 'horizontal arrangement' of the apparatus.

All parts of the apparatus, next to the membranes may be made of glass. Preferably, the apparatus is made of three separate parts only: cover, first compartment and third compartment, wherein the separate parts may be mounted to each other preferably in an air-tight manner. Also the apparatus as shown in FIG. 9 is preferably made of glass.

Figure 9:
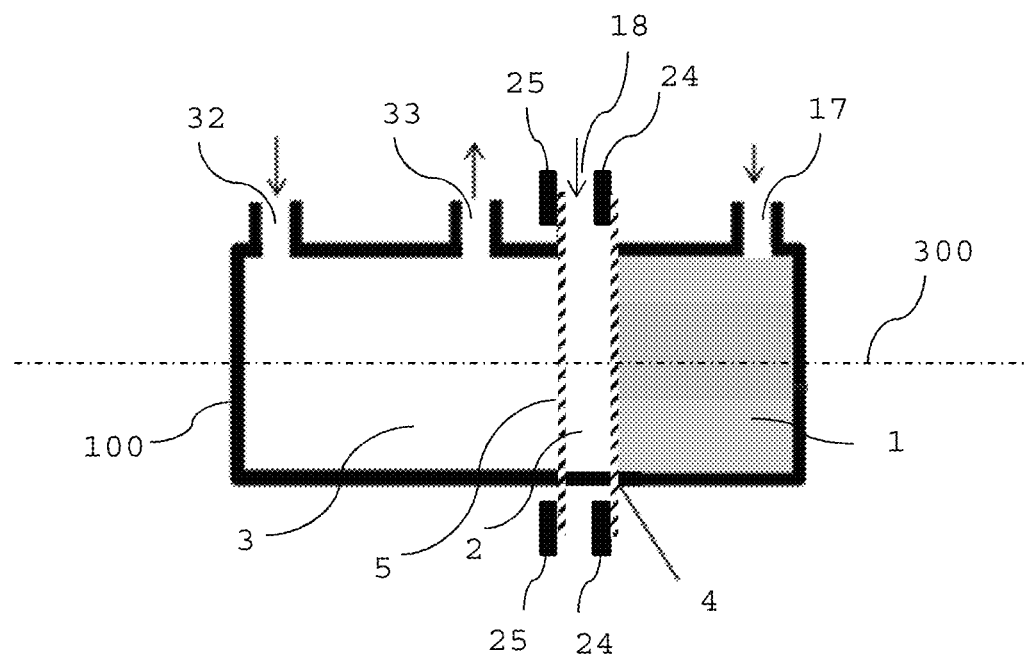
FIG. 9 shows a schematic illustration of a second embodiment of the apparatus according to the invention.

The apparatus of FIG. 9 comprises a receptacle 100, for example of cuboid or tubular form. A first semi-permeable membrane 4 and a second semi-permeable membrane 5 are arranged in the receptacle such as to divide the interior of the receptacle 100 in a first compartment 1, a second compartment 2 and a third compartment 3. The first 4 and the second 4 semi-permeable membrane 5 are arranged vertically in the receptacle 100 and perpendicular to a longitudinal axis 300 of the receptacle 100.

The first compartment 1 comprises a first inlet 17 arranged on top of the receptacle 100 for supplying a first fluid, for example, vitreous humor into the first compartment 1. One side wall of the first compartment 1 is formed by the first semi-permeable membrane 4.

The two semi-permeable membranes 4,5 are arranged distanced to each other, forming the second compartment 2 between the two membranes. A distance between the membranes 4,5 may be varied, for example, adapted to a physiological system to be simulated. Preferably, first and second membrane 4,5 have a predefined distance between the membranes, preferably over the entire extension of the membranes. The second compartment 2 comprises a second inlet 18 arranged on top of the receptacle 100 for supplying a gel matrix into and removing same from the second compartment 2.

The third compartment 3 is formed as a flow-through chamber comprising inlet and outlet 32,33, which are arranged in FIG. 9 on top of the receptacle 100 for supplying and removing a third fluid, for example, a buffer solution. However, inlet and outlet may also be arranged in preferably different (solid) side walls of the third compartment. One side wall of the third compartment 3 (not formed by a receptacle wall) is formed by the second semi-permeable membrane 5.

The three compartments 1, 2, 3, are arranged next to each other in a side-by-side manner. The semi-permeable membranes 4,5 are arranged vertically in the receptacle forming a 'vertical arrangement' of the apparatus.

The semi-permeable membranes 4,5 are held by holders 24,25. The holders 24,25 are arranged on the top and below the bottom of the receptacle 100 outside of the receptacle 100. The holders 24,25 may also be arranged circumferentially around the receptacle 100. The holders may, for example, be clamps.

Figure 10A:
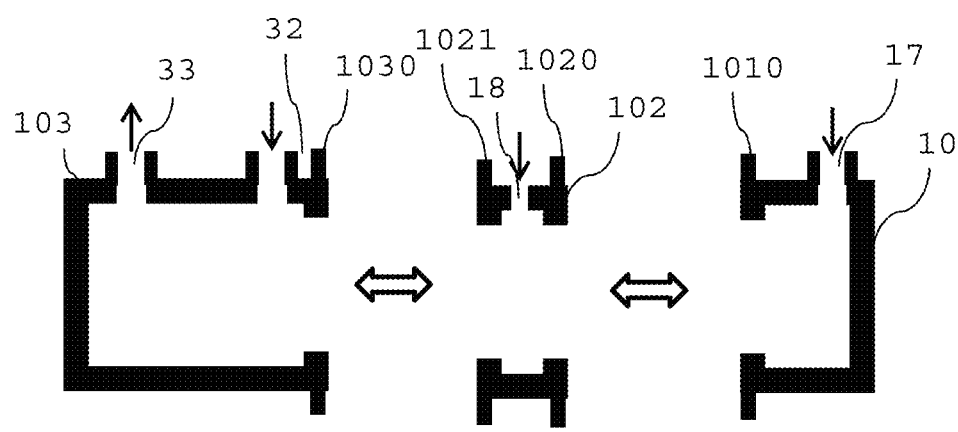
FIGS. 10a, 10b show a variant of the embodiment of the apparatus of FIG. 9.
Figure 10B:
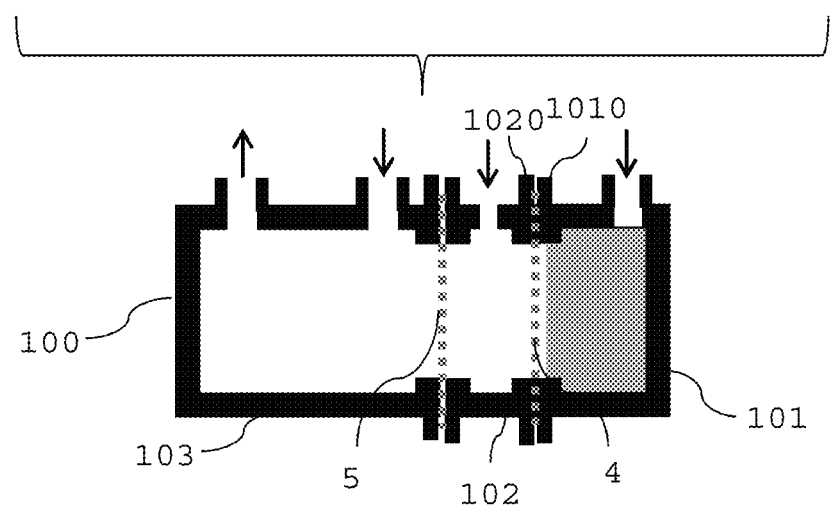

A clamping of the membranes 4,5 may also be achieved by the receptacle 100 itself. For example, the receptacle 100 may be made of several, for example, three parts. A semi-permeable membrane may then be clamped between two parts upon mounting and fixing the parts to each other. Each part then basically forms a compartment. Such an embodiment of the apparatus is illustrated in FIG. 10a and FIG. 10b. FIG. 10a shows the individual three parts 101, 102, 103 of the receptacle 100, which may be mounted to the apparatus according to the invention with a first semi-permeable membrane 4 clamped between first and second part 101,102 and with a second semi-permeable membrane 5 clamped between second and third part 102,103. Each two parts of the receptacle may be provided with clamping means (not shown) for holding the two parts to each other and for achieving a liquid tight connection between the two parts. To support clamping, each part 101, 102, 103 is provided with circumferentially running rims 1010, 1020, 1021, 1030. In the mounted state of the receptacle, shown in FIG. 10b, each two rims 1010,1020; 1021,1030 come to lie against each other, clamping the semi-permeable membrane along a ring portion. Preferably, clamping means are provided to clamp each two rim portions.

Preferably, the semi-permeable membranes 4,5 are plane membranes. However, if the material of the membranes allows, the membranes may also be pre-shaped, for example, concave or convex to simulate the geometry of portions of an eyeball. Preferably, the forms of the semi-permeable membranes 4,5 correspond to each other. While vertically arranged membranes are preferably held in the receptacle by clamping or other holding means, the first and second membranes 4, 5 may also be supported by respective first and second supports forming compartment walls as described above with respect to FIGS. 8a-8e. Holders 24,25 may then be omitted.

A substance, for example macromolecules, may be injected through the first opening 17 into the first fluid in the first compartment 1. It migrates to all sides. Due to gravitational force, migration to the bottom of the first compartment is preferred. However, the bottom being formed by a closed receptacle wall does not allow diffusion of the substance out of the first fluid through the bottom. Only upon migration of the substance to the first semi-permeable membrane 4, a diffusion out of the first compartment, through the first membrane 4, into and through the gel matrix in the second compartment 2, through the second membrane and into the buffer solution in the third compartment 3 occurs. Inlet 17, as well as the inlet and outlet 32,33 of the third compartment also allow the extraction of samples for analysing purposes.

The invention has been described relating to specific embodiments. However, further embodiments may be realized without departing from the scope of the invention. For example, form and size of the apparatus may be adapted to a specific application a substance shall be tested for. Especially, a geometry of the apparatus may be varied. For example, compartments and membranes may be arranged in an essentially flat manner, such that the apparatus is formed by a stack of compartment separated by the membranes. The geometry of an arrangement may also have influence on the materials used in the method and apparatus according to the invention. For example, in a flat configuration, a substance may provide sufficient support for a membrane such that for example a first support may possibly be omitted or limited to small edge portions. In addition, the fluid or semi-fluid material of the gel matrix may be replaced by a porous solid material forming the barrier. For example, open-pored ceramic or open plastic materials may be favorable when combined with cell growth in the barrier material. Yet further one membrane may be replaced by two or more membranes having the same or different MWCOs.

The invention claimed is:

1. An apparatus for analyzing the behaviour of molecules in simulated physiological environment, the apparatus comprising
   a first compartment for receiving a first fluid,
   a second compartment for receiving a gel matrix, and
   a third compartment for receiving a second fluid; the apparatus further comprising
   at least one first semi-permeable membrane, and
   at least one second semi-permeable membrane, the at least one second semi-permeable membrane being arranged at a distance from the at least one first semi-permeable membrane, wherein
   the at least one first semi-permeable membrane is arranged between the first compartment and the second compartment, and wherein the at least one second semi-permeable membrane is arranged between the second compartment and the third compartment, wherein the first compartment, the second compartment and the third compartment are arranged in a row, and wherein the at least one first semi-permeable membrane and the at least one second semi-permeable membrane are arranged substantially vertically between the respective compartments, the apparatus further comprising holders for holding the at least one first semi-permeable membrane and the at least one second semi-permeable membrane between the respective compartments, and wherein the holders do not extend into any of the first, second or third compartment.

2. The apparatus according to claim 1, wherein a Molecular Weight Cut Off (MWCO) of the at least one first semi-permeable membrane substantially corresponds to the Retinal Exclusion Limit (REL).

3. The apparatus according to claim 1, wherein the at least one first semi-permeable membrane has a Molecular Weight Cut Off (MWCO) being smaller than or equal to the Molecular Weight Cut Off (MWCO) of the at least one second semi-permeable membrane.

4. The apparatus according to claim 1, wherein the at least one first semi-permeable membrane has a concave shape.

5. The apparatus according to claim 1, wherein the at least one second semi-permeable membrane has a concave shape.

6. The apparatus according to claim 1, comprising or being made of glass.

7. The apparatus according to claim 1, further comprising a first support for supporting the at least one first semi-permeable membrane.

8. The apparatus according to claim 7, wherein the first support has a concave shape.

9. The apparatus according to claim 1, further comprising a second support for supporting the at least one second semi-permeable membrane.

10. The apparatus according to claim 9, wherein the second support has a concave shape.

11. The apparatus according to claim 1, wherein the first compartment comprises the first fluid, which first fluid is vitreous humor.

12. The apparatus according to claim 1, wherein the third compartment comprises the second fluid, which second fluid is a buffer solution.

13. The apparatus according to claim 12, wherein the buffer solution is a physiologically relevant buffer solution.

14. A method of using the apparatus according to claim 1 for in vitro testing a substance for determining stability or bioavailability of the substance, comprising:
   providing the apparatus of claim 1;
   providing a first fluid, a gel matrix and a second fluid;
   separating the first fluid and the gel matrix by at least one first semi-permeable membrane;
   separating the gel matrix and the second fluid by at least one second semi-permeable membrane;
   injecting a substance into the first fluid;
   letting the substance migrate from the first fluid through the at least one first semi-permeable membrane, through the gel matrix, through the at least one second semi-permeable membrane and into the second fluid;
   removing a sample from the first fluid and from the second fluid; and
   measuring the substance concentration in the first fluid, in the second fluid or in both, the first and the second fluid, wherein the measurements are performed over several hours up to one or two weeks or longer.

15. The method of claim 14, wherein the substance is a drug formulation.

16. The method of claim 14, wherein the substance comprises molecules having a size in a range between about 1 kDa and about 250 kDa.

17. The method of claim 14, wherein the substance comprises molecules having a size in a range between 4 kDa and 150 kDa.

* * * * *